US006423311B1

(12) United States Patent
Mardiney, III et al.

(10) Patent No.: US 6,423,311 B1
(45) Date of Patent: *Jul. 23, 2002

(54) METHOD OF DECREASING RADIATION OR RADIO-MIMETIC CHEMOTHERAPY FOR HEMATOPOIETIC PLURIPOTENT CELL ENGRAFTMENT

(75) Inventors: Michael Mardiney, III, Baltimore; Harry L. Malech, Bethesda, both of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/468,727

(22) Filed: Dec. 21, 1999

Related U.S. Application Data

(60) Provisional application No. 60/001,386, filed on Jul. 21, 1995.

(51) Int. Cl.$^7$ .......................... A01N 63/00; C12P 21/02; C12N 5/00; C12N 5/08; A61N 1/30; A61K 38/00

(52) U.S. Cl. ..................... 424/93.7; 435/69.5; 435/325; 435/372; 604/20; 514/12

(58) Field of Search ........................... 514/12; 435/69.5, 435/69.7, 325, 372; 604/19, 20; 424/93.7

(56) References Cited

U.S. PATENT DOCUMENTS

| 5,004,681 | A |   | 4/1991  | Boyse et al. .................... 435/2 |
| 5,078,996 | A |   | 1/1992  | Conlon, III et al. ....... 424/85.1 |
| 5,106,733 | A |   | 4/1992  | Baker et al. ................ 435/69.5 |
| 5,843,423 | A | * | 12/1998 | Lyman et al. |
| 6,103,694 | A | * | 8/2000  | Mardiney, III et al. ....... 514/12 |

FOREIGN PATENT DOCUMENTS

| EP | 0 627 487 A2 | * | 5/1994 |
| JP |       065602 |   | 3/1995 |
| WO |   WO92/21402 |   | 12/1992 |

OTHER PUBLICATIONS

Cobbold et al. "Monoclonal antibodies to promote marrow engraftment and tissue graft tolerance", *Nature*, 323:164–166, 1992.

Colson, et al. "A nonlethal conditioning approach to achieve durable multilineage mixed chimerism and tolerance across major, minor and hematopoietic histocompatability barriers", *J. Immunol.*, 155:4179–4188, 1995.

(List continued on next page.)

*Primary Examiner*—James Ketter
*Assistant Examiner*—Q Janice Li
(74) *Attorney, Agent, or Firm*—Needle & Rosenberg, P.C.

(57) ABSTRACT

The present invention provides a method of engrafting donor mammalian hematopoietic pluripotent cells in a mammalian recipient using a decreased amount of radiation, comprising: (a) administering to the recipient at least one dosage of a hematopoietic growth factor; (b) subjecting the recipient to a low dosage of radiation; and (c) transplanting the donor hematopoietic pluripotent cells in the recipient, thereby engrafting the donor mammalian hematopoietic pluripotent cells in the mammalian recipient using a decreased amount of radiation. The invention also provides a method of engrafting donor mammalian hematopoietic pluripotent cells in a mammalian recipient using a decreased amount of radiomimetic compound, comprising: (a) administering to the recipient at least one dosage of a hematopoietic growth factor; (b) subjecting the recipient to a low dosage of radiomimetic compound; and (c) transplanting the donor hematopoietic pluripotent cells in the recipient, thereby engrafting the donor mammalian hematopoietic pluripotent cells in the mammalian recipient using a decreased amount of radiomimetic compound.

8 Claims, 1 Drawing Sheet

OTHER PUBLICATIONS

Manual of Oncology Therapeutics, See–Lasley (Ed.), The C.V. Mosby Co., St. Louis, pp. 17, 88 and 104, 1981.

Moore et al. "Synergy of interleukin 1 and granulocyte colony–stimulating factor: In vivo Stimulation of stem–cell recovery and hematopoietic regeneration following 5–fluorouracil treatment of mice" *Proc. Natl. Acad. Sci. USA*, 84:7134–7138, 1987.

Rosenzweig et al. "Efficient and durable gene marking of hematopoietic progenitor cells in non–human primates after non–ablative conditioning" *Blood*, 94(7):2271–86, 1999.

Sheridan et al. "Effect of peripheral–blood progenitor cells mobilised by filgrastim (G–CSF) on platelet recovery after high–dose chemotherapy" *The Lancet*, 339:640–644, 1992.

R Storb et al., Blood, "DLA–Identical bone marrow grafts after low–dose total body irradiation: The effect of canine recombinant hematopoietic growth factors," Nov. 1994, vol. 84, No. 10, pp. 3558–3566.*

Down et al., "Transient and permanent engraftment potential of murine hematopoietic stem cell subsets: differential effects of host conditioning with gamma radiation and cytotoxic drugs," *Exp. Hem.* 21:913–921 (1993).

Tavassoli, M., "The role of conditioning regimens in homing of transplanted hemopoietic cell," *Bone Marrow Transplantation* 10:15–17 (1992).

Mauch, P. et al., "Hematopoietic stem cell compartment: acute and late effects of radiation therapy and chemotherapy," *Int. J. Radiation Oncology Biol. Phys.*, 31(5):1319–1339 (1995).

Uckun, F. et al., "in vivo radioprotective effects of recombinant human granulocyte colony–stimulating factor in lethally irradiated mice," *Blood*, 75:638–645 (1990).

Weaver, C.H. et al., "Phase I Study of high–dose busulfan, melphalan and thiotepa with autologous stem cell support in patients with refractory malignancies," *Bone Marrow Transplantation*, 14:813–819 (1994).

Faucher, C. et al., "Comparison of G–CSF–primed peripheral blood progenitor cell and bone marrow auto transplantation: clinical assessment and cost–effectiveness," *Bone Marrow Transplantation*, 14:895–901 (1994).

Vose, J.M. et al. "Clinical applications of hematopoietic growth factors," *J. Clin. Oncology*, 13(4):1023–1035 (1995).

Wilson et al., "Interleukin–I administration before high–dose ifosamide (I), CBDCA (C), and etoposide (E) (ICE) with autologous bone marrow shortens neutrophil recovery: a phase I/II study," *Proc. Am. Soc. Clin. Oncol.*, 12:937a (1993).

Talmadge, J.E., "The combination of stem cell transplantation and immunotherapy: future potential," *In vivo*, 8:675–690 (1994).

Juttner, C.A. et al., "Blood cell transplantation: report from an international consensus meeting, " *Bone Marrow Transplantation*, 14:689–693 (1994).

George, J. M., "The present and future of hematopoietic cytokines in clinical practice," *Polyfunctionality of Hematopoietic Regulators: The Metcalf Forum. Stem Cells*, 12(supp I):249–255 (1994).

Nemunaitis, J., "Biological activities of hematopoietic growth factors that lead to future clinical application," *Cancer Investigation*, 12(5):516–529 (1994).

\* cited by examiner

METHOD OF DECREASING RADIATION OR RADIO-MIMETIC CHEMOTHERAPY FOR HEMATOPOIETIC PLURIPOTENT CELL ENGRAFTMENT

This application claims priority to U.S. patent application Ser. No. 08/983,532, filed Apr. 10, 1998, now U.S. Pat. No. 6,103,694, which is a 35 U.S.C. §371 patent application of PCT/US96/12368, filed Jul. 22, 1996, from U.S. provisional patent application Serial No. 60/001,386 which was filed on Jul. 21, 1995, which applications are hereby incorporated herein by reference in their entirety.

BACKGROUND OF THE INVENTION

1. Field of the Invention

The present invention relates to the field of improving the engraftment of hematopoietic stem and progenitor cells in human recipients to treat disease. The invention also relates to a method for decreasing radiation or chemotherapy for hematopoietic pluripotent cell engraftment.

2. Background Art

The practice of bone marrow transplantation (BMT) or peripheral blood stem cell transplantation (PBSCT) involves placing a suspension of donor hematopoietic pluripotent cells (HPCs) into the blood stream of the recipient. HPC transplantations are currently performed with a recipient pre-conditioning regimen of high dosage radiation and/or chemotherapy. The goal of these treatments is to create an environment in the recipient in which the donor's HPCs can successfully engraft by homing into the recipient's bone marrow to further undergo hematopoiesis. There may be several objectives for the use of such pre-conditioning regimens, including eliminating cells underlying diseases such as leukemia, or lymphoma, or serving an immunosuppressive function to mitigate graft rejection in the treatment of non-cancerous diseases. Conditioning regimens overall have the desirable effect of eradicating endogenous HPCs to make available more homing sites for transplanted HPCs to successfully engraft. It is believed that current radiation treatments allow homing and engraftment of transplanted stem cells by directly damaging or depleting the recipient's own stem cells, other hematopoietic regulatory cells, bone marrow stroma, and/or the microcirculatory system. Tavassoli, M., "The role of conditioning regimens in homing of transplanted hemopoietic cell," *Bone Marrow Transplantation*, 10:15–17 (1992).

In clinical practice, radiation has been used primarily in high doses to eliminate cells underlying cancerous diseases and to immunosuppress graft rejection. Currently, patients are irradiated with approximately 500 to 1600 cGy at single doses or in fractions. However, the use of radiation can have lethal toxic effects in the recipient, due to the depletion of mature functional blood cells and damage to other organ systems. Therefore, non-myeloablative pre-transplantation regimens, which both minimize radiation effects and attain effective levels of engraftment, are very desirable.

SUMMARY OF THE INVENTION

The present invention provides a method of engrafting donor mammalian hematopoietic pluripotent cells in a mammalian recipient using a decreased amount of radiation, comprising: a. administering to the recipient at least one dosage of a hematopoietic growth factor; b. subjecting the recipient to a low dosage of radiation; and, c. transplanting the donor hematopoietic pluripotent cells into the recipient, thereby engrafting the donor mammalian hematopoietic pluripotent cells in the mammalian recipient using a decreased amount of radiation.

The invention also provides a method of engrafting donor mammalian hematopoietic pluripotent cells in a mammalian recipient using a decreased amount of radiomimetic compound, comprising: a. administering to the recipient at least one dosage of a hematopoietic growth factor; b. subjecting the recipient to a low dosage of radiomimetic compound; and, c. transplanting the hematopoietic pluripotent cells into the recipient, thereby engrafting the donor mammalian hematopoietic pluripotent cells in the mammalian recipient using a decreased amount of radio-mimetic compound.

DETAILED DESCRIPTION OF THE INVENTION

Figure 1:
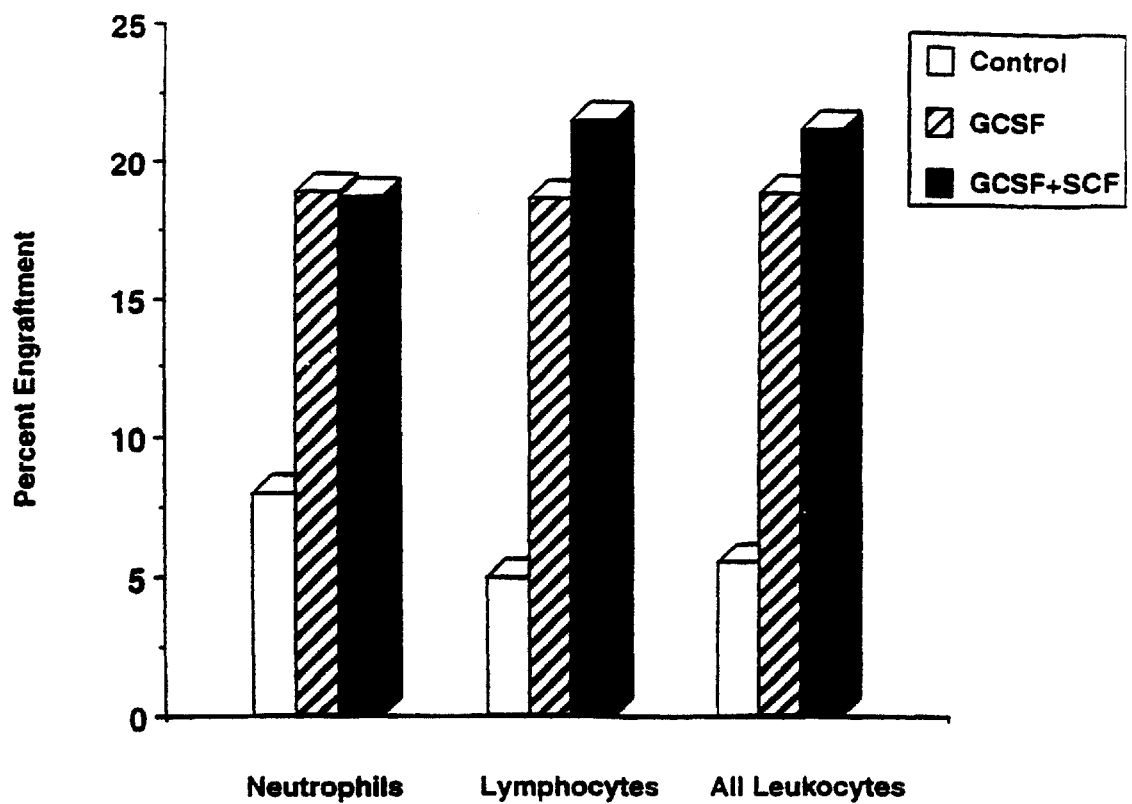
FIG. 1 is a bar graph showing the cytokine hematopoietic growth factor pre-treatment conditioning effect on engraftment of HPCs following 200 cGy radiation in mice, one month after transplantation. Recipient C57BL/6J-Ly-5.1-Pep$^{3b}$ mice received b.i.d. sc injections of PBS (□) 0.1% BSA, 4 μg rhGCSF (□) in 0.1% BSA, or 4 μg rhGCSF plus 1.0 μg rmSCF(■) in 0.1% BSA (R&D Systems, Minneapolis, Minn.) for four days. On the fifth day, mice received a single sc injection followed one hour later by a 200 cGy radiation dose. Four hours after irradiation, all mice received 0.5×10$^6$ Sca-1+ BM cells via tail vein injection. Mice were bled 1 month after BMT and PB was analyzed for engraftment. Both treatment groups demonstrated at least a 3 fold increase in engraftment compared with controls ($p<0.01$). The data represent three experiments in series with 2 mice per condition in each experiment. All animals survived this procedure.

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein are hereby incorporated in their entireties by reference.

As used in the claims, "a" may mean one or more than one, depending upon the context within which it is used. The term "hematopoietic pluripotent cells" (HPCs) is used herein to describe both undifferentiated stem cells or partially committed progenitor cells which would be transferred in either a bone marrow transplantation (BMT) or a peripheral blood stem cell transplantation (PBSCT). BMT techniques are very well-established. Methods to obtain purified hematopoietic stem cells are also well-known. See for example: U.S. Pat. Nos. 5,061,620; 5,087,570; 4,714,680; and 4,965,204.

The present invention provides a method of engrafting donor mammalian hematopoietic pluripotent cells in a mammalian recipient using a decreased amount of radiation, comprising: a. administering to the recipient at least one dosage of a hematopoietic growth factor; b. subjecting the recipient to a low dosage of radiation; and, c. transplanting the donor hematopoietic pluripotent cells into the recipient, thereby engrafting the donor mammalian hematopoietic pluripotent cells in the mammalian recipient using a decreased amount of radiation. General cellular transplantation techniques are generally followed with the use of the recipient pre-conditioning as described herein. Preferably, the transplantation is autologous or allogenic. However, the transplantation can also be xenogenic. Such transplantation may require the additional use of immunosuppressive compounds.

Hematopoietic growth factors are glycoprotein cytokines that regulate the proliferation and differentiation of hematopoietic progenitor cells. The hematopoietic growth factors intended to be used in the present invention can be selected from the group GCSF (granulocyte colony stimulating factor), SCF (stem cell factor), GMCSF (granulocyte macrophage colony stimulating factor), IL-1 (interleukin-1), IL-3, IL-6, IL-8, IL-11, IL-12, LIF (leukemia inhibitory factor), FGF-$\beta$ (fibroblast growth factor $\beta$), FLT3, or a combination thereof. These growth factors can be purchased (e.g. R&D Systems, Minneapolis, Minn.) or made following procedures set forth in the art generally and in publications describing the factors. Additionally, the hematopoietic growth factor can be a modified form of the factor or a fusion protein of hematopoietic growth factors selected from the group GCSF, SCF, GMCSF, IL-1, IL-3, IL-6, IL-8, IL-11, IL-12, LIF, FGF-$\beta$, and FLT3. For example, PIXY321 is a fusion protein of GMSCF and IL-3. Modified growth factors (e.g. muteins) and fusion proteins can be made according to methods known in the art. See, e.g. (Sambrook et al., *Molecular Cloning: A Laboratory Manual*, 2nd Ed., Cold Spring Harbor Laboratory, Cold Spring Harbor, N.Y., 1989). Hematopoietic growth factors, fusion, modifications, and combinations can be pre-screened for efficacy in the methods set forth in the Examples.

The hematopoietic growth factor can be administered to the recipient over a period ranging from about one day to two weeks prior to radiation or the administration of radiomimetic compounds. More preferably, the hematopoietic growth factor can be administered to the recipient over about a five day period. The hematopoietic growth factor administered is preferably from about 0.1 to 200 $\mu$g/kg/day for about five days prior to subjecting the recipient to the low dosage of radiation or radio-mimetic compound. Determining the exact dosage of hematopoietic growth factor depends upon the type of cytokine being administered, and the condition of the patient, among other factors known to the skilled artisan. See, e.g., *Remington's Pharmaceutical Sciences*, latest edition, by E.W. Martin Mack Pub. Co., Easton, Pa.

The step of subjecting the recipient to low dosage radiation can also be performed within about the same day as the final hematopoietic growth factor administration. The low dosage radiation is preferably from about 10 to 500 cGy, and more preferably, is about a 200 cGy dosage.

The transplantation of hematopoietic pluripotent cells in mice is preferably a transplantation of about 0.5×10$^6$ SCA-1+ cells. The transplantation of hematopoietic pluripotent cells in humans is preferably a transplantation of about 10 to 500×10$^6$ CD34+ cells.

The invention also provides a method of engrafting donor mammalian hematopoietic pluripotent cells in a mammalian recipient using a decreased amount of radiomimetic compound, comprising: a. administering to the recipient at least one dosage of a hematopoietic growth factor; b. subjecting the recipient to a low dosage of radio-mimetic compound; and, c. transplanting the hematopoietic pluripotent cells into the recipient, thereby engrafting the donor mammalian hematopoietic pluripotent cells in the mammalian recipient using a decreased amount of radio-mimetic compound. In this method, the presently preferred radio-mimetic compounds are busulfan or BCNU, or a combination thereof. The radio-mimetic compound can be administered at a dosage ranging from $LD_{0.1}$ to $LD_{50}$. See e.g. Down et al. "Transient and permanent engraftment potential of murine hematopoietic stem cell subsets: differential effects of host conditioning with gamma radiation and cytotoxic drugs," *Exp. Hem.* 21:913–921 (1993).

Allogenic and autologous HPC transplantation currently utilizes recipient pre-conditioning consisting of ablative radiation and/or chemotherapy to ensure successful engraftment of donor stem cells. Typically, transplantations are performed as a rescue strategy following high-dose ablation for cancer therapy in the autologous setting, or as an engraftment strategy following high-dose ablation for immunological suppression in the allogenic setting. At the doses required, these current therapies have significant multiorgan toxic effects.

Many diseases treatable with HPC transplantation do not require high dose ablation, however high dose ablation has previously been required to obtain suitable HPC engraftment. The present discovery permits improved HPC engraftment in patients without the need to administer life threatening levels of ablative therapy. This invention can greatly improve the survival and cure rates of numerous hematopoietic diseases which do not require high dose ablation which currently rely on the transplantation of HPCs. For example, diseases and conditions which can be treated by the methods of the present invention include: congenital B- and T-lymphocyte disorders, such as predominantly antibody defects, X-linked agammaglobulinemia, common variable immunodeficiency, immunodeficiency with thymoma, selective IgA deficiency, X-linked immunodeficiency with hyper-IgM, antibody deficiency with normal immunoglobulins, subclass deficiency, poor response to polysaccharide antigens, or X-linked lymphoproliferative syndrome; or a combined immunodeficiency-primary defect in cellular immunity, such as severe combined immunodeficiency, autosomal recessive and X-linked, adenosine deaminase deficiency, defective expression of histocompatibility antigens, deficiency of T-cell receptors, Omen's syndrome, cellular immunodeficiency with immunoglobulins (Nezelof's syndrome), purine nucleoside phosphorylase deficiency; or an immune deficiency associated with other defects, such as Wiskoff-Aldrich syndrome, ataxia telangiectasia, cartilage-hair hypoplasia, hyperimmunoglobulin E syndrome, or chronic mucocutaneous candidiasis. The invention may treat disorders of phagocytic function, such as disorders of production and consumption, abnormal production, Kostmann's syndrome, Schwachman's syndrome, cyclic neutropenia, Primary B- and T-lymphocyte disorders, X-linked hyper-IgM, X-linked agammaglobulinemia, ataxia telangiectasia, cartilage-hair hypoplasia, IgA deficiency; disorders of migration and chemotaxis, general defects in leukocyte mobility, nonspecific disorders, such as Kartogener's syndrome, lazy leukocyte syndrome, hyper-IgE syndrome, Chédiak-Higashi syndrome; or disorders of intracellular killing, such as chronic granulomatous disease, myeloperoxidase deficiency, gluthathione reductase and peroxidase deficiency, glucose-o-phosphate dehydrogenase deficiency; or a deficiency of leukocyte function antigen 1 (LFA-1).

The invention can also be useful for indications for bone marrow transplantation, such as hematologic disorders, marrow aplasia, Fanconi's aplasia, Diamond-Blackfan syndrome, hemoglobinopathies, $\beta$-thalassemia major, sickle cell anemia, neutrophil disorders, congenital neutropenia, chronic granulomatous disease, Chédiak-Higashi syndrome, Osteopetrosis; immune deficiency disorders, such as severe combined immunodeficiency disease, ADA-deficient SCID, reticular dysgenesis, bare lymphocyte syndrome, PNP deficiency, LFA-1 deficiency, ataxia telangiectasia, or Wiskoff-Aldrich syndrome; metabolic disorders, such as mucopolysaccharidoses, Hurler's syndrome, Hunter's syndrome, Sanfilippo's syndrome, leukodystrophies, metachromatic leukodystrophy, adrenoleucodystrophy, sphingolipidoses, Neimann-Pick syndrome, Gaucher's disease; or in the setting of HIV infection, red cell membrane disorders (such as hereditary spherocytosis, etc.), G-6-PD deficiency, paroxysmal nocturnal hemoglobinuria, myelodysplastic syndrome, or aplastic anemia, for example. Furthermore, the discovery has useful implications for improving the efficacy of gene therapies using HPCs, especially in those contexts where less than 100% HPC replacement is required for effectiveness.

The growth factors used in the invention can be conveniently formulated into pharmaceutical compositions composed of one or more of the compounds in association with a pharmaceutically acceptable carrier. See, e.g., *Remington's Pharmaceutical Sciences,* referenced above, which discloses typical carriers and conventional methods of preparing pharmaceutical compositions that may be used in conjunction with the preparation of formulations of the inventive compounds and which is incorporated by reference herein. By "pharmaceutically acceptable" is meant a material that is not biologically or otherwise undesirable, i.e., the material may be administered to an individual along with the growth factor without causing any undesirable biological effects or interacting in a deleterious manner with any of the other components of the pharmaceutical composition in which it is contained.

The growth factors may be administered orally, parenterally (e.g., intravenously), by intramuscular injection, by intraperitoneal injection, topically, transdermally, or the like, although subcutaneous injection is preferred. The amount of active compound administered will, of course, be dependent on the subject being treated, the subject's weight, the manner of administration and the judgment of the prescribing physician. Generally, however, administration and dosage will approximate that which is typical for the administration of naturally occurring proteins, especially hematopoietic growth factors. The optimal dosages of the particular hematopoietic growth factors may routinely be determined by a skilled artisan using currently available techniques and references.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected hematopoietic growth factors in combination with a pharmaceutically acceptable carrier and, in addition, may include other medicinal agents, pharmaceutical agents, carriers, adjuvants, diluents, etc.

Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see *Remington's Pharmaceutical Sciences,* referenced above.

Parental administration is generally characterized by injection. Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, etc.) but some errors and deviations should be accounted for.

The data which forms the basis of the present invention concerns the enhanced in vivo transfer of purified SCA-1+ bone marrow derived HPCs using congenic C57BL/6 mice, which differ only at the Ly5 locus. The origin of a cell is detectable by immunoreactivity with either anti-Ly5.1 or anti-Ly5.2 antibodies by FACS of PBMCs. See, e.g. Flemming et al., "Functional Heterogeneity is associated with the cell cycle status of murine hematopoietic stem cells," *J. Cell Biol.* 122(4):897–902 (1993); Wineman et al., "CD4 is expressed on murine pluripotent hematopoietic stem cells," *Blood* 80(7):1717–1724 (1992); Wineman et al., "Maintenance of high levels of pluripotent hematopoietic stem cells in vitro: effect of stromal cells and c-kit," *Amer. Soc. Hem.* (1993). Using this system, the effects of pre-transplantation cytokine conditioning on short term engraftment, defined as the percentage of total PBMCs in the recipient that were donor Ly5.2 cells, measured one month after transplantation, have been determined.

Recipient C57BL/6-Ly-5.1-Pep$^{3b}$ mice received twice daily subcutaneous injections of either vehicle control (0.1%BSA), 4 µg (about 200 µg/kg) recombinant human granulocyte colony stimulating factor (rhGCSF) (R&D Systems Minneapolis, Minn.) in 0.1%BSA, or 4 µg rhGCSF+ 1.0 µg (about 50 µg/kg) recombinant murine stem cell factor (rmSCF) (R&D Systems Minneapolis, Minn.) in 0.1%BSA, for four days. On the fifth day, all mice received a final injection of hematopoietic growth factor or control, and within the about one hour a 200 cGy irradiation dose followed about four hours later by transplantation of $0.5 \times 10^6$ donor Sca-1+ HPC via tail vein injection. Cytokine treatment ceased after transplantation. After one month, mice were bled and those receiving rhGCSF or rhGCSF+rmSCF showed at least a three fold increase in engraftment compared with those receiving control (18.9% and 20.6% versus 5.6%), as shown in FIG. 1. All animals remained healthy during the 1 month of observation reported herein.

What is claimed is:

1. A method of engrafting donor mammalian hematopoietic pluripotent cells in a mammalian recipient using a non-myeloablative amount of radiation, comprising:
   a) administering to the recipient at least one dosage of a hematopoietic growth factor selected from the group consisting of granulocyte colony stimulating factor (GCSF), stem cell factor (SCF), granulocyte macrophage colony stimulating factor (GMCSF), interleukin-1 (IL-1), interleukin-3 (IL-3), interleukin-6 (IL-6), interleukin-8 (IL-8), interleukin-11 (IL-11), interleukin-12 (IL-12), leukemia inhibitory factor (LIF), fibroblast growth factor-β (FGF-β) and FMS-like tyrosine kinase 3-ligand (FLT3-ligand), or a combination thereof;
   b) subjecting the recipient to the non-myeloablative amount of radiation; and
   c) transplanting the donor hematopoietic pluripotent cells into the recipient, thereby engrafting the donor mammalian hematopoietic pluripotent cells in the mammalian recipient using a non-myeloablative amount of radiation.

2. A method of engrafting donor mammalian hematopoietic pluripotent cells in a mammalian recipient using a non-myeloablative amount of radiation, comprising:
   a) administering to the recipient at least one dosage of a hematopoietic growth factor fuision protein comprising hematopoietic growth factors selected from the group consisting of GCSF, SCF, GMCSF, IL-1, IL-3, IL-6, IL-8, IL-11, IL-12, LIF, FGF-β, and FLT3-ligand;
   b) subjecting the recipient to the non-myeloablative amount of radiation; and
   c) transplanting the donor heinatopoietic pluripotent cells into the recipient, thereby engrafting the donor mammalian hematopoietic pluripotent cells in the mammalian recipient using a non-myeloablative amount of radiation.

3. A method of engraving autologous mammalian hematopoietic pluripotent cells in a mammalian patient using a non-myeloablative amount of radiation, comprising:
   a) administering to the patient at least one dosage of a hematopoietic growth factor selected from the group consisting of GCSF, SCF, GMCSF, IL-1, IL-3, IL-6, IL-8, IL-11, IL-12, LIF, FGF-β, and FLT3-ligand, or a combination thereof;
   b) subjecting the patient to the non-myeloablative amount of radiation; and
   c) transplanting the hematopoietic pluripotent cells into the patient, thereby engrafting the autologous mammalian hematopoietic pluripotent cells in the patient using a non-myeloablative amount of radiation.

4. A method of engrafting autologous mammalian hematopoietic pluripotent cells in a mammalian patient using a non-myeloablative amount of radiation, comprising;
   a) administering to the patient at least one dosage of a hematopoietic growth factor fusion protein comprising hemnatopoietic growth factors selected from the group consisting of GCSF, SCF, GMCSF, IL-1, IL-3, IL-6, IL-8, IL-11, IL-12, LIF, FGF-β, and FLT3-ligand;
   b) subjecting the patient to the non-myeloablative amount of radiation; and
   c) transplanting the hematopoietic pluripotent cells into the patient, thereby engrafting the autologous mammalian hematopoietic pluripotent cells in the patient using a non-myeloablative amount of radiation.

5. The method of claim 1, wherein the non-myeloablative amount of radiation is from about 10 to 500 cGy.

6. The method of claim 2, wherein the non-myeloablative amount of radiation is from about 10 to 500 cGy.

7. The method of claim 3, wherein the non-myeloablative amount of radiation is from about 10 to 500 cGy.

8. The method of claim 4, wherein the non-myeloablative amount of radiation is from about 10 to 500 cGy.

* * * * *